US009814419B2

(12) United States Patent
Karp et al.

(10) Patent No.: US 9,814,419 B2
(45) Date of Patent: Nov. 14, 2017

(54) PULSE OXIMETRY DEVICES AND SYSTEMS AND METHODS OF MAKING THE SAME

(71) Applicant: General Electric Company, Schenectady, NY (US)

(72) Inventors: Jason Harris Karp, Niskayuna, NY (US); Christopher James Kapusta, Delanson, NY (US); Paul Jeffrey Gillespie, Charlton, NY (US); Christopher Fred Keimel, Niskayuna, NY (US); Jeffrey Michael Ashe, Gloversville, NY (US); James Enrico Sabatini, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 3 days.

(21) Appl. No.: 15/092,655

(22) Filed: Apr. 7, 2016

(65) Prior Publication Data
US 2016/0220158 A1 Aug. 4, 2016

Related U.S. Application Data

(62) Division of application No. 14/079,660, filed on Nov. 14, 2013, now abandoned.

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0002* (2013.01); *A61B 5/6826* (2013.01);
(Continued)

(58) Field of Classification Search
CPC .............. A61B 5/1455; A61B 5/14551; A61B 5/14552; A61B 5/14553; A61B 2562/00;
(Continued)

(56) References Cited

U.S. PATENT DOCUMENTS 5,520,177 A * 5/1996 Ogawa ............... A61B 5/14552
600/323
2002/0165440 A1* 11/2002 Mason ............... A61B 5/14552
600/344
(Continued)

*Primary Examiner* — Eric Winakur
*Assistant Examiner* — Chu Chuan (JJ) Liu
(74) *Attorney, Agent, or Firm* — Pabitra K. Chakrabarti

(57) ABSTRACT

An array of emitters includes a device substrate having first and second sides, a thermally and electrically conductive layer disposed on the first side of the device substrate, and an interconnect layer disposed on a first plurality of portions of the second side of the device substrate. The array of the emitters further includes a plurality of emitters disposed in a second plurality of portions of the device substrate, where the plurality of emitters is electrically coupled to the thermally and electrically conductive layer. Also, the array of the emitters includes a plurality of wirebond contacts configured to electrically couple a portion of the interconnect layer to a corresponding emitter of the plurality of emitters, and a plurality of encapsulations, where one or more encapsulations of the plurality of encapsulations are disposed on at least a portion of a corresponding wirebond contact of the plurality of wirebond contacts.

19 Claims, 10 Drawing Sheets

(51) Int. Cl.
  *A61B 5/029* (2006.01)
  *A61B 5/08* (2006.01)
  *H01L 25/075* (2006.01)
  *H05K 1/18* (2006.01)
  *H01L 33/62* (2010.01)

(52) U.S. Cl.
  CPC .............. *A61B 5/742* (2013.01); *A61B 5/029* (2013.01); *A61B 5/0816* (2013.01); *A61B 2562/0238* (2013.01); *A61B 2562/046* (2013.01); *A61B 2562/12* (2013.01); *A61B 2562/164* (2013.01); *A61B 2562/222* (2013.01); *A61B 2562/227* (2013.01); *H01L 25/0753* (2013.01); *H01L 33/62* (2013.01); *H01L 2224/48091* (2013.01); *H01L 2224/73265* (2013.01); *H01L 2224/92247* (2013.01); *H01L 2924/181* (2013.01); *H05K 1/189* (2013.01); *H05K 2201/10106* (2013.01); *H05K 2201/10151* (2013.01); *Y10T 29/49139* (2015.01)

(58) Field of Classification Search
  CPC ........ A61B 2562/02; A61B 2562/0233; A61B 2562/04; A61B 2562/046; A61B 2562/164
  See application file for complete search history.

(56) References Cited

U.S. PATENT DOCUMENTS

| | | | |
|---|---|---|---|
| 2006/0211922 A1* | 9/2006 | Al-Ali | A61B 5/14552 600/310 |
| 2008/0225523 A1* | 9/2008 | De Samber | F21K 9/00 362/249.01 |
| 2009/0237897 A1* | 9/2009 | Ratcliffe | H01L 23/5389 361/760 |

* cited by examiner

PULSE OXIMETRY DEVICES AND SYSTEMS AND METHODS OF MAKING THE SAME

CROSS-REFERENCE TO RELATED APPLICATIONS

This is a Divisional of U.S. patent application Ser. No. 14/079,660, which was filed on Nov. 14, 2013, and entitled, "ARRAYS OF EMITTERS FOR PULSE OXIMETRY DEVICES AND METHODS OF MAKING THE SAME," which is hereby incorporated by reference in its entirely.

This invention was made with Government support under grant number W81XWH1110833 POC awarded by the U.S. Army. The Government has certain rights in the invention.

BACKGROUND

The embodiments of the specification elate to pulse oximetry devices, and more particularly to pulse oximetry devices having arrays of emitters.

Early detection of low blood oxygen is critical in a wide variety of medical applications. For example, in case of insufficient supply of oxygen to a patient during critical care or surgical applications, the risk of permanent brain damage or death may increase. Pulse oximetry is a non-invasive procedure for measuring an oxygen saturation level of arterial blood, which is an indicator of a blood oxygenation. In pulse oximetry measurements, two or more wavelengths of light are passed through a portion of a body of the patient, where the portion of the body contains arterial blood flow. Absorption differences in the two or more wavelengths of light during systolic and diastolic cardiac states are used to determine the blood oxygen concentration.

A pulse oximeter, also known as a pulse oximetry device, uses an optical sensor to measure the blood oxygen saturation as well as pulse rates and degree of perfusion. In operation, pulse oximeters are typically attached to a tissue site on patient's body part having the arterial blood flow. By way of example, the pulse oximeters may be attached to a finger, earlobe, or foot of the patient. In instances where the pulse oximeter is attached to the finger, a sensor of the pulse oximeter is disposed on one side of the finger such that emitters of the sensor project light through outer tissues of the finger and into blood vessels and capillaries present in the finger. A photodiode positioned opposite to the emitters is configured to detect emitted light emerging from the outer tissues of the finger. The photodiode generates a signal based on the detected emitted light. The photodiode then transmits that signal to a processor of the pulse oximeter. The processor determines blood oxygen saturation by computing a differential absorption by the arterial blood of the two or more wavelengths (e.g., red and infrared) emitted by the sensor.

Existing pulse oximetry devices typically employ clamp on designs for the pulse oximeters. The clamp on designs have a rigid and non-flexible body.

BRIEF DESCRIPTION

In one embodiment, an array of emitters is provided. The array of emitters includes a device substrate having a first side and a second side, a thermally and electrically conductive layer disposed on the first side of the device substrate, and an interconnect layer disposed on a first plurality of portions of the second side of the device substrate. The array of emitters further includes a plurality of emitters disposed in a second plurality of portions of the device substrate, where the plurality of emitters is electrically coupled to the thermally and electrically conductive layer. Also, the array of emitters includes a plurality of wirebond contacts configured to electrically couple a portion of an interconnect layer to a corresponding emitter of the plurality of emitters, and a plurality of encapsulations, where one or more encapsulations of the plurality of encapsulations are disposed on at least a portion of a corresponding wirebond contact of the plurality of wirebond contacts and the emitters of the plurality of emitters.

In another embodiment, a pulse oximetry system having a pulse oximetry device is provided. The pulse oximetry device includes a device substrate having a first side and a second side, a thermally and electrically conductive layer disposed on the first side of the device substrate, an interconnect layer disposed on the second side of the device substrate, and a plurality of arrays of emitters disposed on the second side of the device substrate, wherein the plurality of arrays of the emitters is electrically coupled to the thermally and electrically conductive layer. Further, the pulse oximetry device includes a plurality of detectors disposed on the second side of the device substrate, and a plurality of wirebond contacts configured to electrically couple a portion of an interconnect layer to a corresponding emitter of the plurality of arrays of the emitters. The plurality of detectors is configured to detect emission signals emitted by one or more emitters of the plurality of arrays of the emitters. The pulse oximetry system further includes a processor configured to process the detected emission signals.

In yet another embodiment, a method of making a pulse oximetry device includes providing a device substrate having a first side and a second side, where a thermally and electrically conductive layer is disposed on at least a portion of the first side of the device substrate. Further, the method includes disposing an interconnect layer on a first plurality of portions of the second side of the device substrate, forming a plurality of cavities in a second plurality of portions on the second side of the device substrate, and disposing one or more emitters in corresponding cavities of the plurality of cavities to form a plurality of arrays of emitters on the second side of the device substrate. Moreover, the method includes providing a plurality of wirebond contacts such that each wirebond contact electrically couples at least a portion of the interconnect layer to a corresponding emitter of the plurality of arrays of the emitters, and disposing a plurality of detectors on the second side of the device substrate.

DRAWINGS

These and other features and aspects of embodiments of the invention will become better understood when the following detailed description is read with reference to the accompanying drawings in which like characters represent like parts throughout the drawings, wherein.

Figure 12:
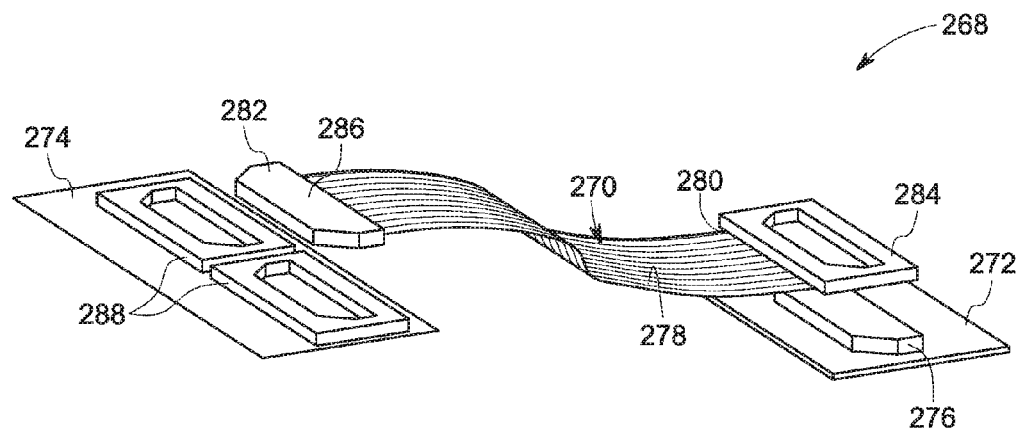
Figure 13:
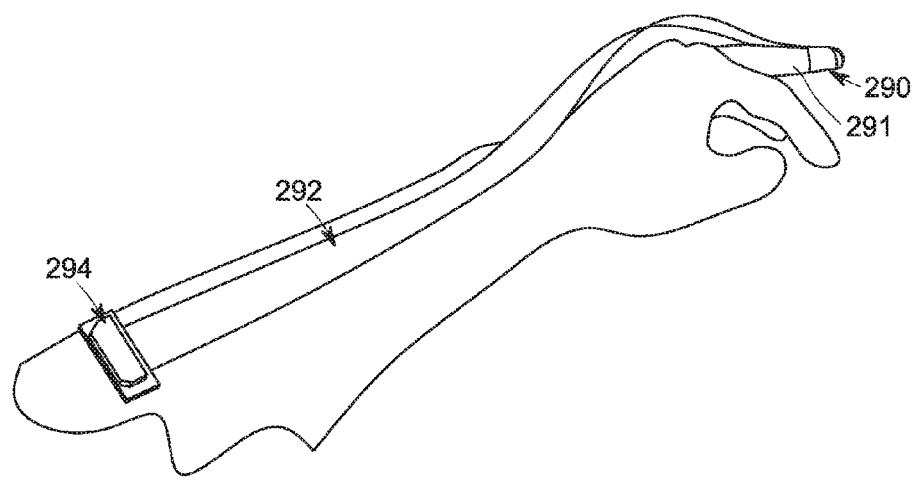

FIG. 12 is a perspective view of an example cable assembly configured to operatively couple a pulse oximetry device to an external device or circuitry, in accordance with aspects of the specification; and FIG. 13 is a perspective view of an example pulse oximetry device operatively coupled to a finger of a patient, where the pulse oximetry device is coupled to the cable assembly of FIG. 12, in accordance with aspects of the specification.

DETAILED DESCRIPTION

In certain embodiments of the specification, a plurality of arrays of emitters and methods of making the same are provided. In certain other embodiments of the specification, pulse oximetry devices employing the plurality of arrays of the emitters are provided. In one embodiment, the plurality of arrays of the emitters may be disposed on a flexible device substrate. Accordingly, the plurality of arrays of the emitters may be configured to be molded into non-flat shapes, as required, without producing undesirable strain in the arrays. Advantageously, the plurality of arrays of the emitters may be bendable to a determined extent without introducing any undesirable strain in the plurality of arrays of the emitters.

In certain embodiments, the array of emitters may be printed on one or more flat, non-flat or flexible surfaces made of materials, such as, but not limited to, polyimide, polyethylene terephthalate (PET) (e.g., biaxially oriented PET), glass, plastic, rubber, metal, or combinations thereof. The array of emitters may be used in various applications, such as, but not limited to, wearable health monitors and biomedical imaging devices. In a particular embodiment, the array of emitters may be used in small sized, wearable electronics. In one example, the wearable electronics may include a pulse oximetry device. The pulse oximetry device may be a part of a pulse oximetry system.

In some embodiments, the pulse oximetry device having the plurality of arrays of the emitters may be a flexible device. Advantageously, as compared to commercially available pulse oximetry devices, the pulse oximetry device of the specification may be configured to be disposed relatively closer to a surface of a portion of a body, where the portion of the body includes a region of interest. For example, the region of interest may include a region in the portion of the body that has arterial blood flow. Non-limiting examples of the portions of the body having the region of interest may include one or more of a finger, an earlobe, or a foot. In one example, the pulse oximetry device may be disposed around a portion of a finger in a fashion similar to disposing a band aid. The flexible nature of the pulse oximetry device of the specification enables the emitters and detectors of the pulse oximetry device to be disposed in close proximity to tissues in the region of interest. Further, the flexible body allows the sensor to be placed on different parts of the body, and may conform to different body shapes as required.

Figure 1:
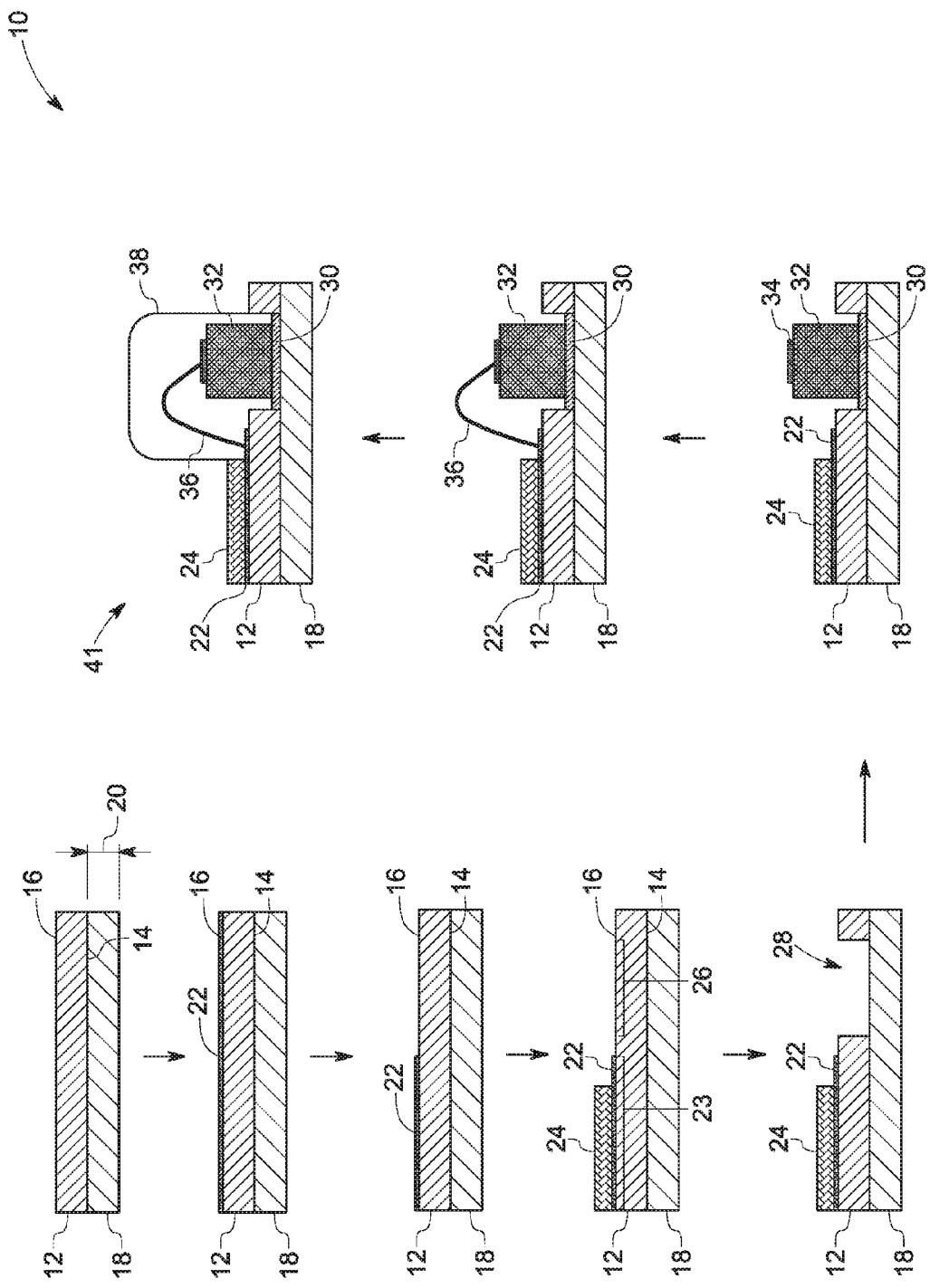
FIG. 1 is a cross-sectional view of an example method of making an array of emitters, in accordance with aspects of the specification.

FIG. 1 illustrates a flow diagram 10 of an example method of making an array of emitters. For ease of representation, and clarity of drawings, in the illustrated flow diagram 10 only a portion of the array of emitters is illustrated. However, it should be noted that remaining portions of the array of emitters may be fabricated using similar or identical process steps. The method may commence by providing a device substrate 12 having a first side 14 and a second side 16. The device substrate 12 may be a flexible device substrate that is configured to bend to a desirable extent. Non-limiting examples of a material of the device substrate 12 may include polymer, rubber, glass, or combinations thereof. In one example, the device substrate 12 may be made of polyimide. In one example, the step of providing the device substrate 12 may include forming a film of the material of the device substrate 12. The techniques for forming the film may include deposition techniques, such as, but not limited to, spray deposition, vapor deposition techniques, plasma assisted deposition techniques, or printing techniques. Non-limiting examples of the printing techniques may include techniques, such as, but not limited to, screen printing for a flat surface, inkjet printing for a flat surface, pad printing for a curved surface, gravure printing, flexographic printing, conventional flex circuit fabrication, printed circuit board fabrication, or combinations thereof.

Next, a thermally and electrically conductive layer 18 is disposed on the first side 14 of the device substrate 12. Non-limiting examples of materials for the thermally and electrically conductive layer 18 may include copper, metal composites of copper, metal composites of copper and molybdenum, metal composites of copper and tungsten, composites of aluminum or copper graphite, copper clad metal alloys, or combinations thereof. In one example, the metal alloys present in the copper clad metal alloys may include one or more of iron, nickel, cobalt or manganese (e.g., copper clad iron-nickel-cobalt alloy). The thermally and electrically conductive layer 18 may be configured to provide an electrical coupling between an emitter 32 and an electrical device (not shown) or an electrical connection (not shown) that is external to the array of emitters. The thermally and electrically conductive layer 18 may be configured to act as a heat sink for the array of emitters. In one embodiment, the thermally and electrically conductive layer 18 may be made of a layered structure having a composition titanium-copper-nickel-gold. A thickness 20 of the thermally and electrically conductive layer 18 may be such that the thermally and electrically conductive layer 18 facilitates heat dissipation. In one example, the thickness 20 of the thermally and electrically conductive layer 18 may be in a range from about 10 microns to about 50 microns. In one embodiment, the step of providing the device substrate 12 may include the step of providing the device substrate 12 having the thermally and electrically conductive layer 18 disposed on the first side 14 of the device substrate 12. In one example, a film of the material of the device substrate 12 may include copper cladding. By way of example, the copper cladding may be formed on the device substrate 12 using metallization.

An interconnect layer 22 may be disposed on at least a portion 23 of the second side 16 of the device substrate 12. Non-limiting examples of the interconnect material may include one or more electrically conductive materials, such as, but not limited to, titanium, copper, nickel, aluminum, or combinations thereof. In one embodiment, the interconnect layer 22 may be a pre-patterned layer that may be disposed on the second side 16 of the device substrate 12. In this embodiment, the patterned layer may be disposed on the portion 23 of the second side 16 of the device substrate 12. In another embodiment, the interconnect layer 22 may be made by forming a layer of interconnect material and patterning the layer of the interconnect material. In this embodiment, the layer of the interconnect material may be disposed on and outside the portion 23 on the second side 16 of the device substrate 12, and then the layer of the interconnect material may be patterned such that the layer of the interconnect material is present only in portion 23 of the second side 16 of the device substrate 12. In one example, the patterning of the layer of interconnect material may be performed using techniques, such as but not limited to, masking, etching, lithography, or combinations thereof. In some embodiments, the interconnect layer 22 may be disposed on the device substrate 12 using deposition techniques, such as, but not limited to, metallization, sputtering, thin film deposition techniques, spraying, or combinations thereof. After disposing the interconnect layer 22, a protective cover 24 may be disposed on at least a portion of the interconnect layer 22. The protective cover 24 may include structures made of electrically non-conductive materials, such as, but not limited to, polyimide coverlay, epoxy solder mask, or combinations thereof.

Subsequent to, or before disposing the interconnect layer 22, protective cover 24, or both, another portion 26 of the device substrate 12 may be processed to form a cavity 28. In one embodiment, the cavity 28 may be formed by employing techniques, such as, but not limited to, etching, masking, ablation, lithography, or combinations thereof. In some embodiments, the cavity 28 may be configured to receive a single emitter 32. Alternatively, in some other embodiments, the cavity 28 may be configured to receive one or more arrays of the emitters. Alternatively, in place of cavities 28, metal pads may be disposed on the first and second sides of the device substrate 12, the metal pads disposed on opposite sides of the device substrate 12 may be coupled using thermal vias.

Next, an electrically conductive coupler 30 is disposed in at least a portion of the cavity 28. Subsequently, an emitter 32 is disposed on at least a portion of the conductive coupler 30 to mechanically couple the emitter 32 to the thermally and electrically conductive layer 18. In one example, the cavity 28 may be a through cavity to provide thermal grounding to the emitter 32 and to provide electrical connection between the emitter 32 and the electrically conductive layer 18. In one embodiment, the electrically conductive coupler 30 may include electrically conductive adhesive, such as, but not limited to, silver epoxy. The electrically conductive coupler 30 may be configured to facilitate thermal conductivity between the emitter 32 and the thermally and electrically conductive layer 18 to enhance thermal dissipation from the array of emitters 32. In another embodiment, the reference numeral 30 may be used to represent a shim or plug or any other like fastener that may be configured to receive and mechanically couple the emitter 32 to the thermally and electrically conductive layer 18 while providing an electrical connection between the emitter 32 and the thermally and electrically conductive layer 18. On one side the emitter 32 is electrically coupled to the thermally and electrically conductive layer 18, while on the other side the emitter 32 may include an electrical contact 34 to facilitate electrical coupling between the emitter 32 and the interconnect layer 22. In one embodiment, the electrical contact 34 may include I/O contact pads that are pre-patterned on the emitter 32.

In embodiments where the electrically conductive coupler 30 includes an electrically conductive adhesive, the electrically conductive adhesive may be configured to form bonds upon exposure to determined environmental conditions, such as, but not limited to, a determined temperature, a determined pressure, or both. In one embodiment, the determined pressure, the determined temperature, cure time, or combinations thereof, may be decided based on chemical composition, viscosity, of the electrically conductive coupler 30. In a non-limiting example, the electrically conductive coupler may be room temperature cured or ultraviolet (UV) light cured adhesive. The electrically conductive coupler 30 may be easy to use and disposed in a portion of the cavity 28 using deposition techniques such as, but not limited to, screen printing, spray deposition, pasting, machine, dispensing, jetting, machine dispensing, stamping, hand applying, or combinations thereof.

As noted above, electrical coupling between the emitter 32 and the thermally and electrically conductive layer 18 is provided via the electrically conductive coupler 30. Further, electrical coupling between the emitter 32 and the interconnect layer 22 is provided via a wirebond contact 36. Advantageously, wirebond contacts are cost-effective, flexible and reliable. The wirebond contact 36 may be formed using one or more of gold, aluminum, copper. In certain embodiments, forming the wirebond contact 36 may include ball bonding, wedge bonding, compliant bonding, or combinations thereof. Bond pads may be formed on the emitter 32, interconnect layer 22, or both as a precursor to forming the wirebond contact 36 between the emitter 32 and the interconnect layer 22. Further, forming the wirebond contact 36 may include applying one or more of heat, pressure, radiation, ultrasonic energy to facilitate coupling of the wirebond contact 36 to the interconnect layer 22 and the electrical contact 34 on the emitter 32.

Subsequent to forming the wirebond contact 36, the wirebond contact 36 and at least a portion of the emitter 32 may be encapsulated using an encapsulation 38 to form a portion 41 of an array of emitters. In some embodiments, the encapsulation 38 may be formed by dispensing an encapsulation material in a desirable location on the device substrate 12 and curing the material for a determined time. In one embodiment, the encapsulation 38 may be made of an electrically non-conductive material, such as, but not limited to, silicone, epoxy, or combinations thereof. In some embodiments, the encapsulation 38 may be made of material that is configured to allow at least a portion of emission signals emitted by the emitter 32 to transmit through the encapsulation 38. By way of example, in instances where a pulse oximetry device employs emitters configured to emit in red and infrared wavelength ranges, the encapsulation 38 may be made of material that is transparent to red and infrared wavelength ranges.

In some embodiments, one or more steps in the method of making the emitter assembly may be performed in parallel. In one embodiment, similar steps for various portions of the array of emitters may be performed in parallel. For example, a step of forming cavities on a device substrate for receiving emitters may be performed in parallel in a single step for all the cavities in a single step instead of forming the cavities in a time sequential manner for different portions of the array. Performing a step for different portions of the array in a parallel fashion may reduce the manufacturing time, thereby making the process time efficient. Further, although not illustrated, the array 10 may include different volumes of the electrically conductive coupler 30 to account for height differences in heights of the emitters 32 disposed in the cavities 28. In one embodiment, the method of making the array of emitters may include roll-to-roll processing.

Figure 2:
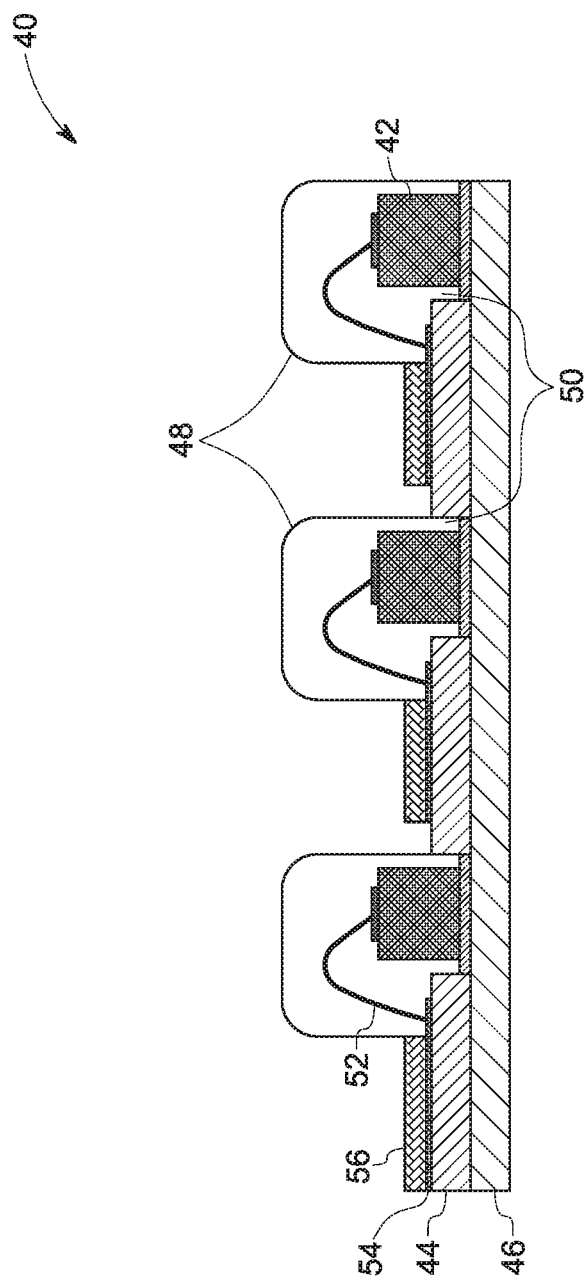
FIG. 2is a cross-sectional view of a portion of an example array of emitters, in accordance with aspects of the specification.
Figure 3:
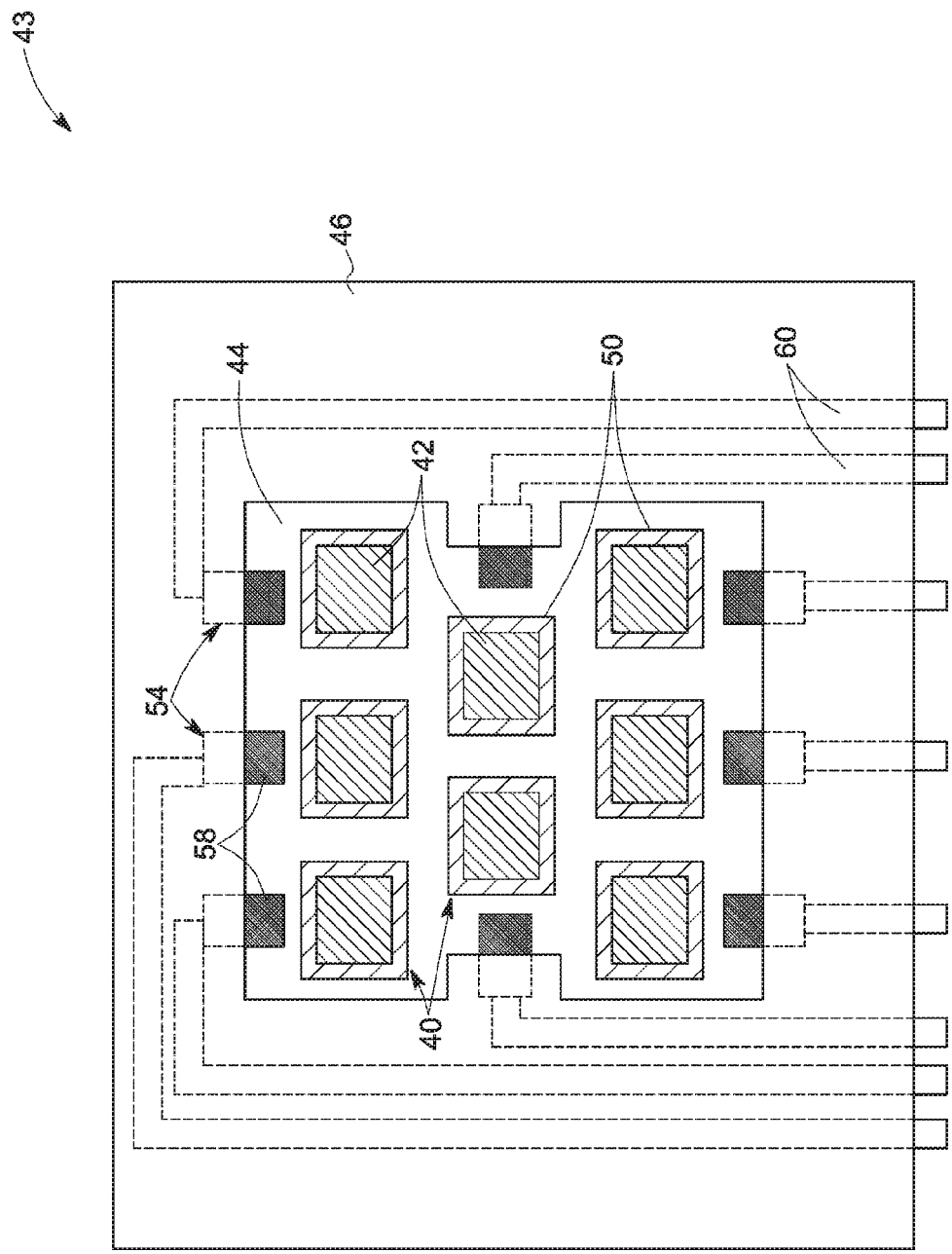
FIG. 3 is a top view of a portion of an example array of emitters having conductive paths configured to connect the emitters of the array of emitters to an external connector, in accordance with aspects of the specification.

FIG. 2 illustrates a cross-sectional view of an example array 40 of emitters 42 having a plurality of emitters 42 disposed in corresponding cavities 50 present in a device substrate 44. FIG. 3 illustrates a top view 43 of the array of the emitters 42 of FIG. 2. The emitters 42 of the array 40 may be of same or different types. Non-limiting examples of the type of emitters 42 may include light emitting diodes, transmitters, photodiodes, or combinations thereof. The emitters 42 of the array 40 may be a part of an emitter drive or detection circuitry. The emitters 42 may be individually and independently controlled using a thermally and electrically conductive layer 46 and an interconnect layer 54. In one embodiment, the array 40 may be a flexible array. A size of the flexible array 40 may be decided based on the application. In one example, the flexible array 40 may include a 4×4 or 6×6 array 40 of the emitters 42. The array 40 of the emitters 42 may be used in diagnostic devices, healthcare systems, monitoring devices, or combinations thereof. In one embodiment, the array 40 of the emitters 42 may be used in wearable monitoring devices. In particular, the array 40 of the emitters 42 may be used in pulse oximetry devices that are wearable. For example, the pulse oximetry device may be configured to be disposed around a portion of a finger of the patient. Light weight and flexible nature of the array 40 of the emitters 42 renders the array 40 suitable for use in wearable monitoring devices, where the devices need to be disposed on a portion of a body for extended periods of time. In certain embodiments, the array 40 of the emitters 42 may be employed in detection devices, such as but not limited to, a pulse oximeter. In certain other embodiments, the array of emitters may be employed in display applications (display products, display emitters, or signage), and light emitters. Advantageously, the array 40 of the emitters 42 is thin, robust and flexible. The flexible array 40 may be thin enough to bend to a desirable extent without introducing any undesirable strains in the array 40.

In the illustrated embodiment, the flexible array may also include a plurality of encapsulations 48, wherein each encapsulation of the plurality of encapsulations 48 is disposed on a corresponding emitter 42 and a corresponding wirebond contact 52 of the plurality of wirebond contacts 52. Moreover, each of the wirebond contact 52 of the plurality of wirebond contacts 52 is configured to electrically couple an emitter 42 of the plurality of emitters 42 to at least a portion of the interconnect layer 54. Each encapsulation 48 may be configured to protect the corresponding emitter 42 and the wirebond contact 52 of the flexible array 40. In one embodiment, the encapsulation 48 may be cured for a determined period of time. In one example, the encapsulation 48 may be exposed to ultraviolet radiation, visible radiation to cure the encapsulation 48. Curing the encapsulation 48 may facilitate mechanical strengthening of the encapsulation 48. In one embodiment, materials for the encapsulation 48 may include resins, such as, but not limited to, epoxy. The material of the encapsulation 48 may be configured to provide electrical isolation to the wirebond contact 52 and also provide the ability to withstand mechanical stress, and thermal shock, without developing any voids or cracks while providing an optically transparent path for the emitters. The array 40 may further include a plurality of protective covers 56 disposed on at least a portion of the interconnect layer 54.

As will be described with respect to FIG. 4, in one embodiment, fewer suitably sized encapsulations may be used in place of the plurality of encapsulations 48 of FIG. 2. By way of example, a larger encapsulation may be used in instances where higher packing density of emitters 42 is desirable in the array 40 of the emitters 42. In one embodiment, a larger encapsulation may be configured to encapsulate an array of emitters and corresponding wirebond contacts.

FIG. 3 illustrates bond pads 58 formed on portions of the interconnect layer 54. The plurality of emitters 42 may be coupled to an external connector (not shown), or device (not shown) via conductive paths or traces 60. The conductive paths 60 are routed out of the array 40 of the emitters 42 to an external connector or other cabling or wireless communication, to connect the array 40 of the emitters 42 to a processor or a user interface. In one embodiment, the plurality of emitters may be operatively coupled to a display device, a processor, a monitoring device, or combinations thereof. Further, as discussed hereinafter with regard to FIG. 4, in some embodiments, a common cavity may be used to dispose the plurality of emitters 42. In this embodiment, a common encapsulation may be used to protect the plurality of emitters disposed in the common cavity.

Figure 4:
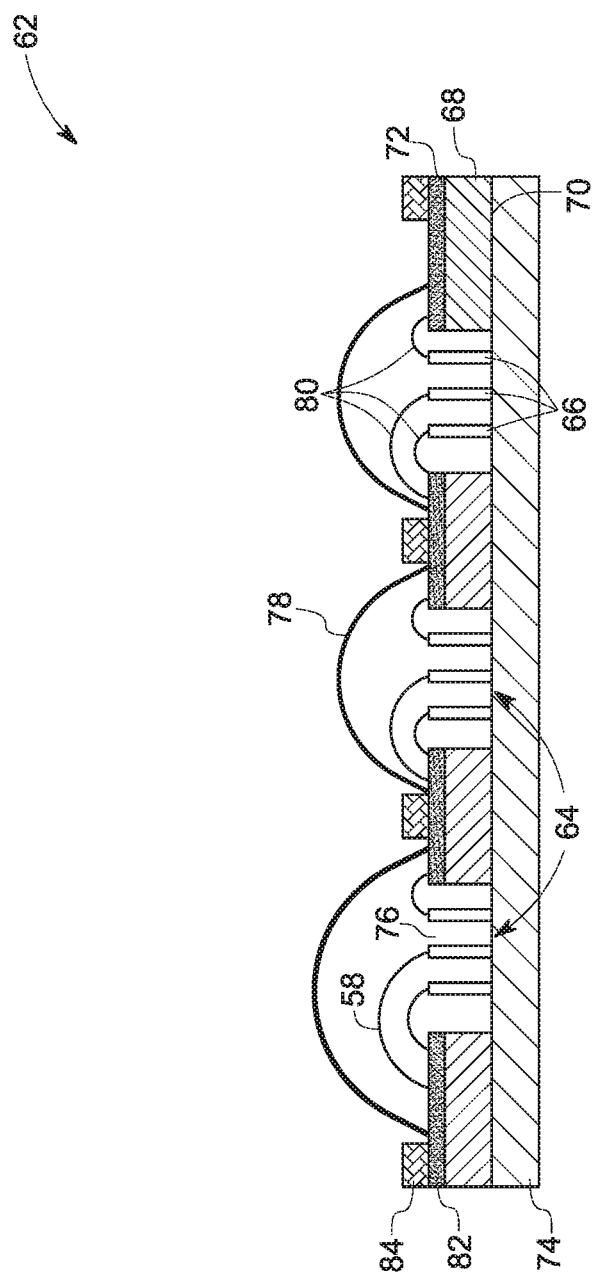
FIG. 4 is a cross-sectional view of a plurality of arrays of emitters disposed on a device substrate, where each array of the plurality of arrays includes a corresponding encapsulation, in accordance with aspects of the specification.

FIG. 4 illustrates a portion 62 of a pulse oximetry device (not shown) having a plurality of arrays 64 of emitters 66. The portion 62 includes a flexible device substrate 68 having a first side 70 and a second side 72. A thermally and electrically conductive layer 74 is disposed on the first side 70 of the flexible device substrate 68. Further a plurality of cavities 76 is formed on the second side 72 of the flexible device substrate 68. Each cavity 76 of the plurality of cavities 76 is a through cavity that extends from the second side 72 of the flexible device substrate 68 to the thermally and electrically conductive layer 74. Further, each cavity 76 of the plurality of cavities 76 is configured to receive an array 64 of the emitters 66. Additionally, the portion 62 includes a plurality of encapsulations 78. Each encapsulation 78 of the plurality of encapsulations is disposed on a cavity 76 of the plurality of cavities 76 such that the encapsulation covers the array 64 and wirebond contacts 80 present in the array 64. Moreover, the portion 62 may include interconnect layer 82 and a protective cover 84. In the illustrated example, the array 64 may be a 3×3 or 4×4 array of light emitting diodes.

Figure 5:
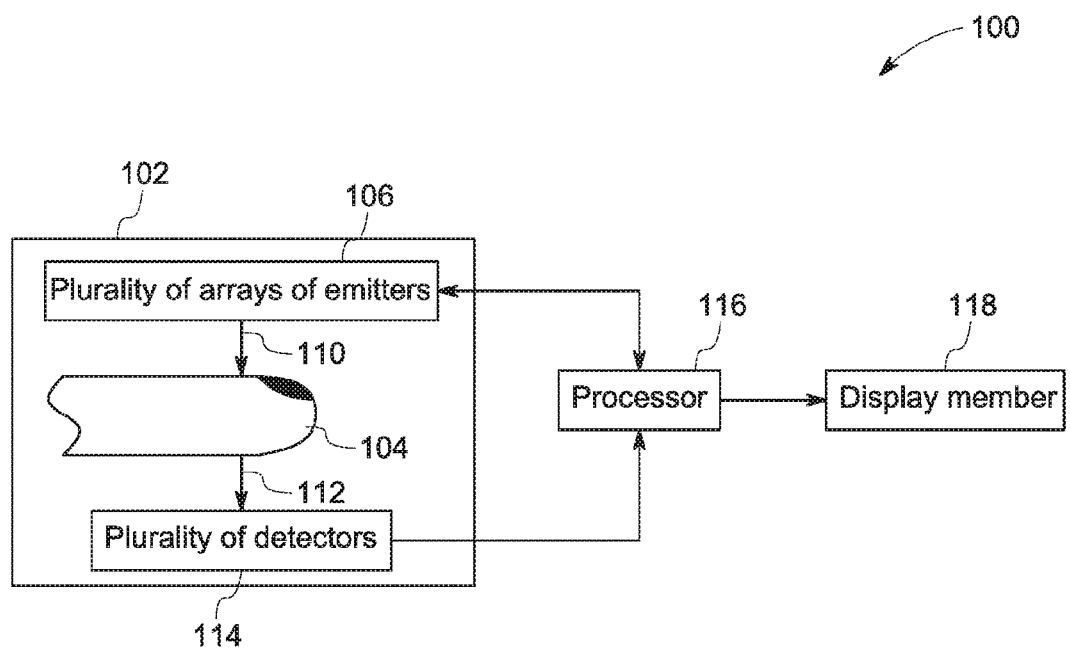
FIG. 5 is a schematic representation of an example pulse oximetry system having a pulse oximetry device, where the pulse oximetry device includes an array of emitters, in accordance with aspects of the specification.

FIG. 5 illustrates an example embodiment of a pulse oximetry system 100 employing a pulse oximetry device 102. The pulse oximetry device 102 is configured to be coupled to a patient (not shown). By way of example, the pulse oximetry device 102 may be configured to be coupled to a fingertip 104 of the patient. Alternatively, the pulse oximetry device 102 may be configured to be coupled to an earlobe, or in the case of an infant, a foot of the infant. Other tissue sites may include the forehead, head, chest, neck or other tissue sites suitable for pulse oximeters with emitters and detectors positioned side by side. In the illustrated embodiment, the pulse oximetry device 102 may include a plurality of arrays of the emitters 106 and a plurality of photodetectors 114. The emitters 106 may be light emitting diodes (not shown). The array of light emitting diodes may be a flexible array. In one example, the emitters 106 may be configured to emit light in two or more wavelengths or wavelength ranges. The light 110 emitted by the emitters 106 may pass through the patient or interact with tissues in a portion of a body of the patient without passing through the body part of the patient. For example, the light 110 may pass through the fingertip 104 of the patient. Alternatively, the light merely interacts with a portion of the tissues present in the fingertip 104 without travelling completely through the fingertip 104. A portion of the light 110 that passes through the fingertip 104 may be absorbed or reflected by the tissues in the fingertip 104 and the remaining portion 112 of the light 110 may be received by the plurality of photodetectors 114. The changing absorbance at each of the wavelengths from the emitters 106 may be measured using the plurality of photodetectors 114. Based on the absorptions measured at the different wavelengths, absorptions due to the pulsing arterial blood may be determined using a processor 116. Advantageously, the absorbance due to arterial blood may exclude absorbance of light due to venous blood, skin, bone, muscle, fat, and other elements, such as nail paint. In one embodiment, based on the absorbance of light by the patient, the processor 116 may be configured to control wavelengths emitted by the emitters 106.

The system 100 may further include a display member 118 configured to display a blood saturation level. Additionally, the display member 118 may be configured to display a plethysmographic waveform of the pulse signal. The plethysmographic waveform may be characterized by two waveforms, namely, a fast frequency waveform that is representative of heart stroke volume, and a slow frequency waveform that is representative of a respiration rate. In one embodiment, the display member 118 may be integral part of the pulse oximetry device 102. Alternatively, in another embodiment, the display member 118 may be external to the pulse oximetry device 102. In this embodiment, the display member 118 may be operatively coupled to the pulse oximetry device 102 using a wired or wireless connection.

Figure 6:
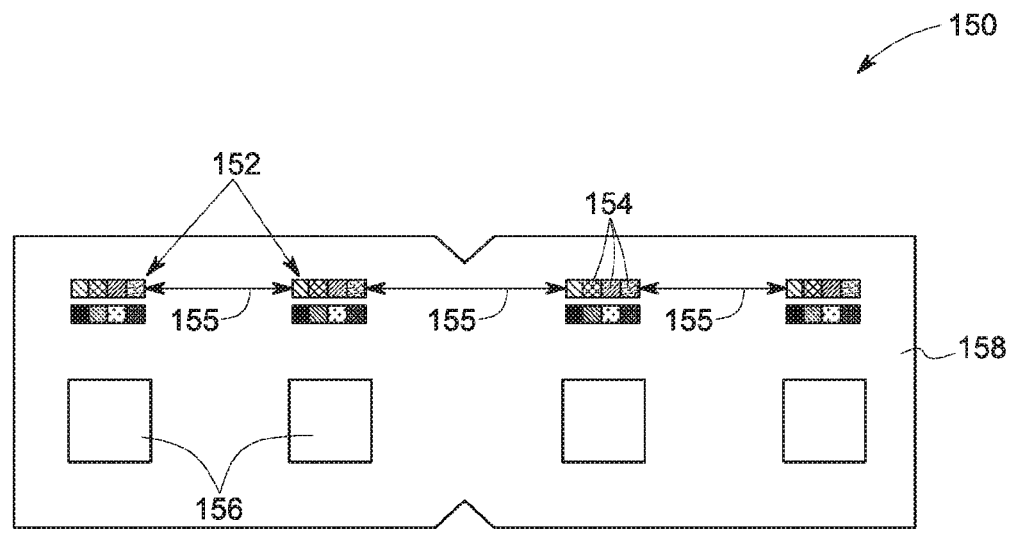
FIG. 6 is a top view of a pulse oximetry device having a plurality of arrays of emitters disposed in a row on a flexible device substrate, and a plurality of detectors disposed in another row on the flexible device substrate, in accordance with aspects of the specification.

FIG. 6 illustrates an example of a pulse oximetry device 150 having a plurality of arrays 152 of emitters and a plurality of detectors 156. In one example, the emitters may be light emitting diodes 154. One or more light emitting diodes 154 of one or more arrays 152 of the plurality of arrays 152 of the light emitting diodes 154 may be configured to emit at wavelengths that are different from wavelengths emitted by other light emitting diodes 154 of the same array 152. In one example, each light emitting diode 154 of an array 152 of 8 light emitting diodes 154 may be configured to emit wavelengths that are different from wavelengths emitted by the other 7 light emitting diodes. In this particular example, the array 152 of the 8 light emitting diodes 154 may be configured to emit 8 different wavelengths. Advantageously, different wavelengths emitted by the different light emitting diodes 154 are capable of detecting absorption differences beyond oxygen saturation and may provide information on total hemoglobin as well as other absorption species.

Emission signals from the different light emitting diodes 154 of the different arrays 152 may be received by one or more detectors 156 of the plurality of detectors. The plurality of arrays 152 of the light emitting diodes 154 and the plurality of detectors 156 may be disposed on a flexible device substrate 158. The light emitting diodes 154 may be disposed on the flexible device substrate 158 using the methods described with respect to FIG. 1. Further, the plurality of detectors 156 may be disposed on the flexible device substrate 158 using the method described with respect to FIG. 1. Alternatively, the plurality of detectors 156 may be disposed on the flexible device substrate 158 using other deposition techniques known in the art. In one embodiment, the plurality of detectors 156 may be disposed on the flexible device substrate 158 such that the plurality of detectors 156 is operatively coupled to a thermally and electrically conductive layer (not shown) disposed on a side of the device substrate 158 that is opposite to the side on which the plurality of arrays 152 of the light emitting diodes 154 and the plurality of detectors 156 are disposed. In the illustrated embodiment of FIG. 6, the layout of the plurality of arrays 152 and the plurality of detectors 156 is such that each array 152 has a detector 156 disposed in parallel opposite to that array 152. The detector 156 disposed in parallel opposite to a particular array 152 may be configured to detect signals from the light emitting diodes 154 of that particular array 152 disposed directly opposite to the detector 156 as well as from light emitting diodes 154 of other arrays 152 of the plurality of arrays 152. Although not illustrated, in an alternate embodiment, the detectors 156 may be disposed such that the arrangement of detectors 156 may be slightly offset with respect to the arrangement of the arrays 152. As with the illustrated embodiment of FIG. 6, in this embodiment also one or more detectors 156 may be configured to detect signals corresponding to one or more light emitting diodes 154 of one or more arrays 152.

In certain embodiments, a distance 155 between any two neighboring arrays 152 may be substantially similar or different. Further, the distance between a detector 156 and one or more arrays 152 may be such that light emitted by the light emitting diodes 154 and reflected or transmitted by the tissues present at different depths may be detected by the detectors 156. The pulse oximetry device 150 may be configured to operate in reflection or transmission mode. In the reflection mode of the device 150, the detectors 156 are configured to acquire emission signals that are scattered out of the patient on the same tissue side as the emitters, i.e., the light emitting diodes 154, but are laterally displaced with respect to the light emitting diodes 154. Whereas, in the transmission mode of the device 150, the detectors 156 are configured to acquire signals that penetrate through the tissues and other physiological structures to reach the detectors 156.

Figure 7:
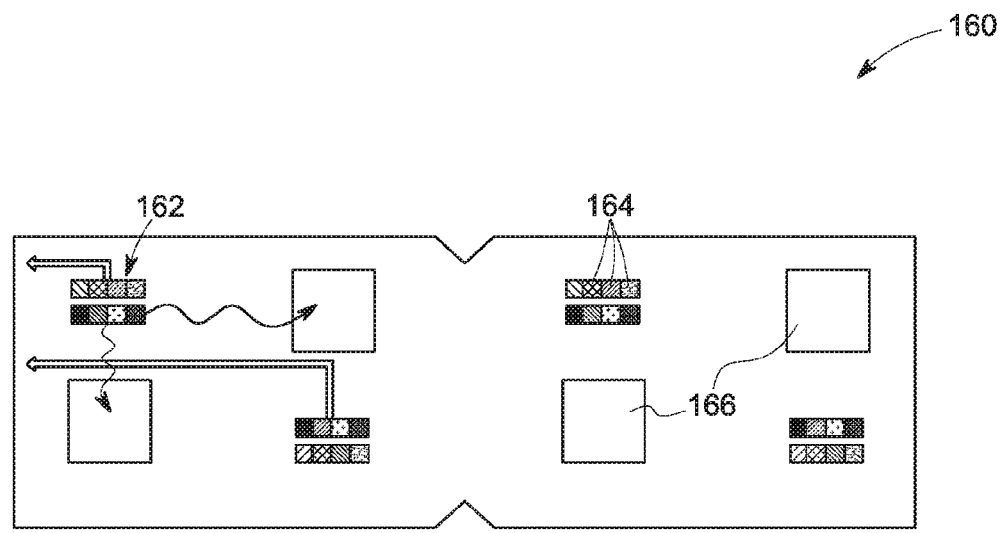
FIG. 7 is a top view of a pulse oximetry device having a plurality of arrays of emitters and a plurality of detectors, where one or more arrays of the plurality of arrays of the emitters and one or more detectors of the plurality of detectors are disposed orthogonally opposite to each other, in accordance with aspects of the specification.

FIG. 7 illustrates another embodiment 160 of the pulse oximetry device 150 of FIG. 6. In the illustrated embodiment, a pulse oximetry device 160 includes an arrangement where a plurality of arrays 162 of emitters 164 and a plurality of detectors 166 may be disposed orthogonally opposite to one another. The pulse oximetry device 160 may be configured to operate in reflection mode, transmission mode, or both.

Figure 8:
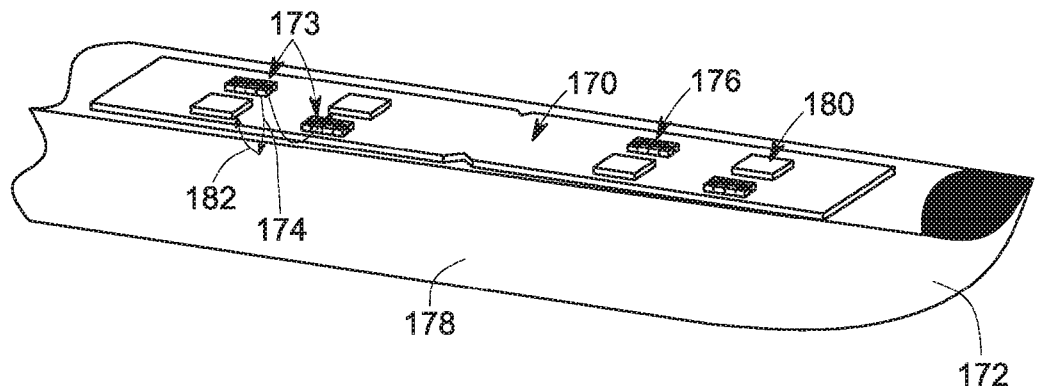
FIG. 8 is a perspective view of an example pulse oximetry device configured to operate in a reflection mode, in accordance with aspects of the specification.

FIG. 8 illustrates an example embodiment of a reflection mode pulse oximetry device 170 disposed on a finger 172 of a patient. It should be noted that the pulse oximetry device 170 may be disposed on any other suitable body part of the patient. In the illustrated embodiment, unlike the currently available, conventional clamp-on pulse oximeters the pulse oximeters device 170 is disposed on only one side of the finger 172 of the patient. When disposed on one side of a portion of the body, such as the finger 172, the pulse oximetry device 170 is configured to operate in the reflection mode. However, when disposed around a portion of a body, the same pulse oximetry device 170 may be configured to operate in a transmission mode, or a combination of reflection and transmission modes. As illustrated, in reflection mode, emission signals 174 emitted by one or more emitters 176 of a plurality of arrays 173 of emitters 176 may be reflected by tissues 178 in the finger 172. The reflected signals 182 are detected by one or more detectors 180 of a plurality of detectors 180. Although not illustrated, different layouts of the plurality of arrays of emitters 176 and the plurality of detectors 180 may be employed in the device 170. For example, the layouts may include the arrays 173 of the emitters 176 and the plurality of detectors 180 disposed in parallel opposite to one another, orthogonally opposite to each other, disposed at an offset from one another, or combinations thereof. In the reflection mode, the pulse oximetry device 170 is designed such that the emitters 176 and the detectors 180 are disposed on the same side of the finger 172. The signals emitted by an emitter 176 may penetrate the tissue 178 in the finger 172 at different depths. The signals 174 closer to the skin may be received by a detector 180 disposed closer to the emitter 176. Similarly, the reflected signals 182 that have penetrated relatively deeper in the finger 172 may be received by a detector 180 disposed farther away from the emitter 176. Accordingly, the plurality of detectors 180 may be used to acquire signals from different depths in the tissue, e.g., the tissue of the finger 172. The plurality of emitters 176 may include a combination of emitters of different wavelengths to facilitate tissue interaction with the emitted signal for tissues disposed at different depths in the region of interest. By way of example, each emitters 176 corresponding to an array of emitters may be configured to emit in a wavelength range that is different from a wavelength range of emission of other emitters 176 in the same array. In one embodiment, a single detector 180 may be used to detect reflected signals 182 corresponding to emission signals 174 from two or more emitters 176 at different tissue depths using time multiplexing.

Figure 9:
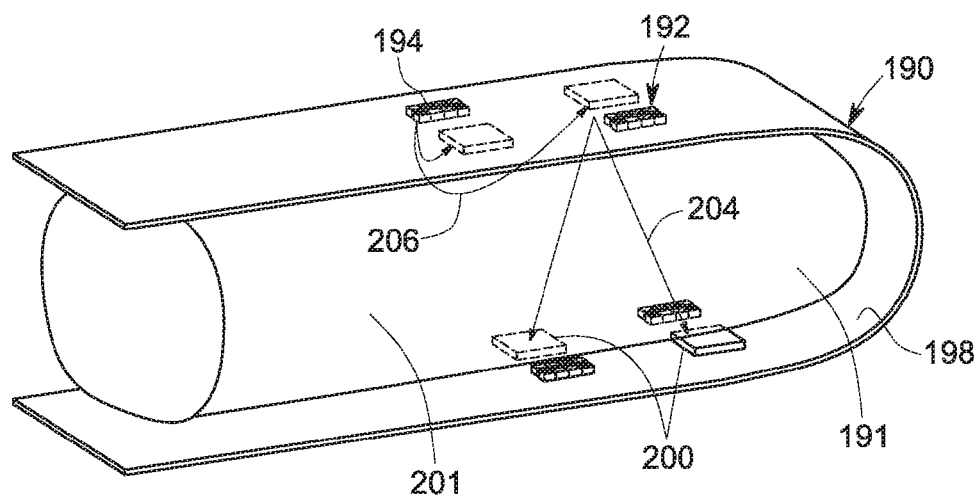
FIG. 9 is a perspective view of a pulse oximetry device in a transmission mode, in accordance with aspects of the specification.

FIG. 9 illustrates an example embodiment of a pulse oximetry device 190 that is configured to operate in both reflection as well as transmission modes. The pulse oximetry device 190 is configured to be at least in part disposed around a portion of a body part, such as a finger 191, from where an oxygen saturation level of blood needs to be measured. As illustrated, a plurality of arrays 192 of emitters 194 is disposed on a flexible device substrate 198. Further, a plurality of detectors 200 is disposed on the flexible device substrate 198. The spacing between the plurality of arrays 192 of the emitters 194, as well as the spacing between the detectors 200 is such that the detectors 200 are configured to acquire signals reflected and transmitted by the tissues in a region of interest 201 in the finger 191. In particular, relative positioning of the emitters 194 and the detectors 200 is such that signals 204 transmitted through the tissues in the region of interest 201 and signals 206 reflected by the tissues in the region of interest 201 may be received by the detectors 200. Although not illustrated, the pulse oximetry device 190 of FIG. 9 may alternatively employ other layouts or arrangements of the arrays 192 of the emitters 194 and the plurality of detectors 200. For example, the layouts may include the arrays 192 of the emitters 194 and the plurality of detectors 200 disposed in parallel opposite to one another, orthogonally opposite to each other, disposed at an offset from one another, or combinations thereof. Additionally, although not illustrated, in one embodiment, the pulse oximetry device 190 of FIG. 9 may employ a plurality of emitters 194 on one side of the finger 191, and a plurality of detectors 200 on another side of the finger 191. In this embodiment, the pulse oximetry device may be configured to operate in transmission mode. Although FIGS. 6-9 are described with respect to a plurality of arrays of the emitters, it should be noted that the emitters may be disposed as a group without any segregation as arrays.

Figure 10:
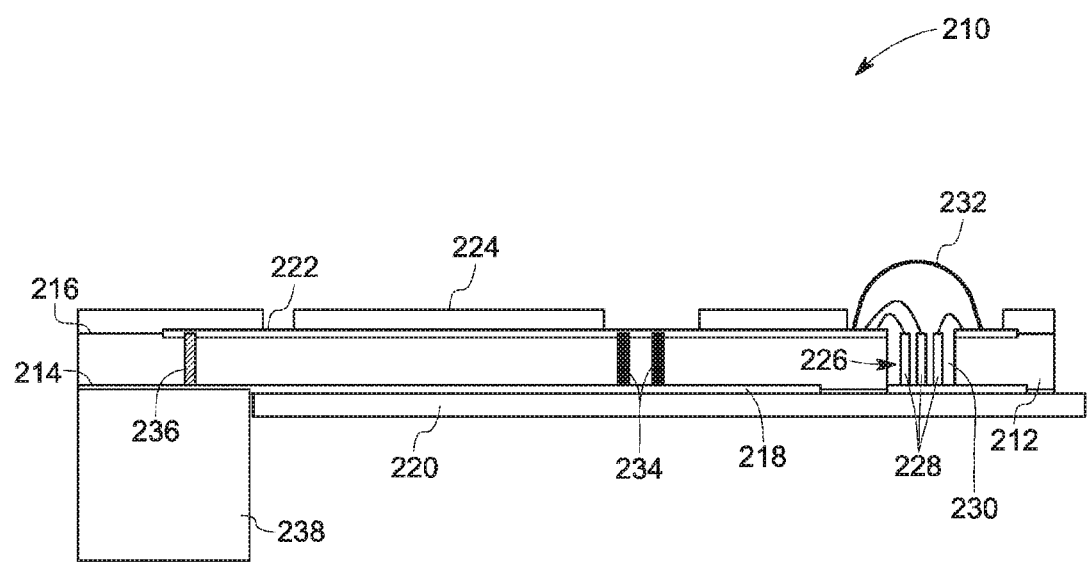
FIG. 10 is a cross-sectional view of a portion of a pulse oximetry device employing an external connector and through vias, in accordance with aspects of the specification.

FIG. 10 illustrates an example of electrical routing components and surface mounted devices disposed in a portion 210 of a pulse oximetry device of the specification. As illustrated, the portion 210 of the pulse oximetry device includes a flexible device substrate 212 having a first side 214 and a second side 216. A thermally and electrically conductive layer 218 may be disposed on the first side 214 of the flexible device substrate 212. A first protective layer 220 may be disposed on at least a portion of the thermally and electrically conductive layer 218. The first protective layer 220 may be made of electrically non-conductive materials. Further, the portion 210 may include an interconnect layer 222 disposed on a portion of the second side 216 of the device substrate 212. Non-limiting examples of the interconnect material may include electrically conductive materials, such as, but not limited to, titanium, copper, nickel, aluminum, or combinations thereof. A second protective cover 224 may be disposed at least on at least a portion of the interconnect layer 222. The protective cover 224 may include structures made of electrically non-conductive materials. In the illustrated embodiment, an array 226 of emitters 228 is disposed in a cavity 230 formed in the device substrate 212. A common encapsulation 232 may be disposed on the emitters 228 of the array 226. Further, the portion 210 may include through vias 234 to provide thermal conductivity paths. The vias 234 may be filled with thermally conductive materials to provide thermally conductive paths. Additionally, the vias 234 may be used to provide electrically conductive paths. In an alternative embodiment, in place of the cavities 230, metal pads may be disposed on the first and second sides 214 and 216 of the device substrate 212, the metal pads disposed on opposite sides of the device substrate 212 and may be coupled using the thermal vias 234. In one example, a via 236 may be used to connect the portion 210 to an external device using an external connector 238. In one embodiment, the external connector 238 may be a surface mounted device. The external connector 238 may be configured to act as an interface between the array of emitters, detectors (not shown) and an electrical device (not shown) or an electrical connection (not shown) that is external to the portion 210. The portion 210 may include an external connector 238 configured to provide electrical connection between the pulse oximetry device and an external component or device. Further, the portion 210 may include a provision 226 for electrically coupling the external connector 238 to an electrical cable (not shown). In certain embodiments, although not illustrated, one or more emitters 228 of the array 226 may be operatively coupled to the thermal vias 234 to facilitate thermal management in the array 226. In some of these embodiments, the one or more emitters 228 of the array 226 may be operatively coupled to the thermal vias 234 using wirebond contacts. The wirebond contacts may be configured to facilitate dissipation of thermal energy from the array 226 by guiding the thermal energy from the array 226 to the thermally and electrically conductive layer 218. In one embodiment, the wirebond contacts coupling the thermal vias 234 and the one or more emitters 228 of the array 226 may be disposed in an encapsulation. By way of example, the encapsulation 232 may be configured to encapsulate the wirebond contacts coupling the thermal vias 234 and the one or more emitters 228 of the array 226.

Figure 11:
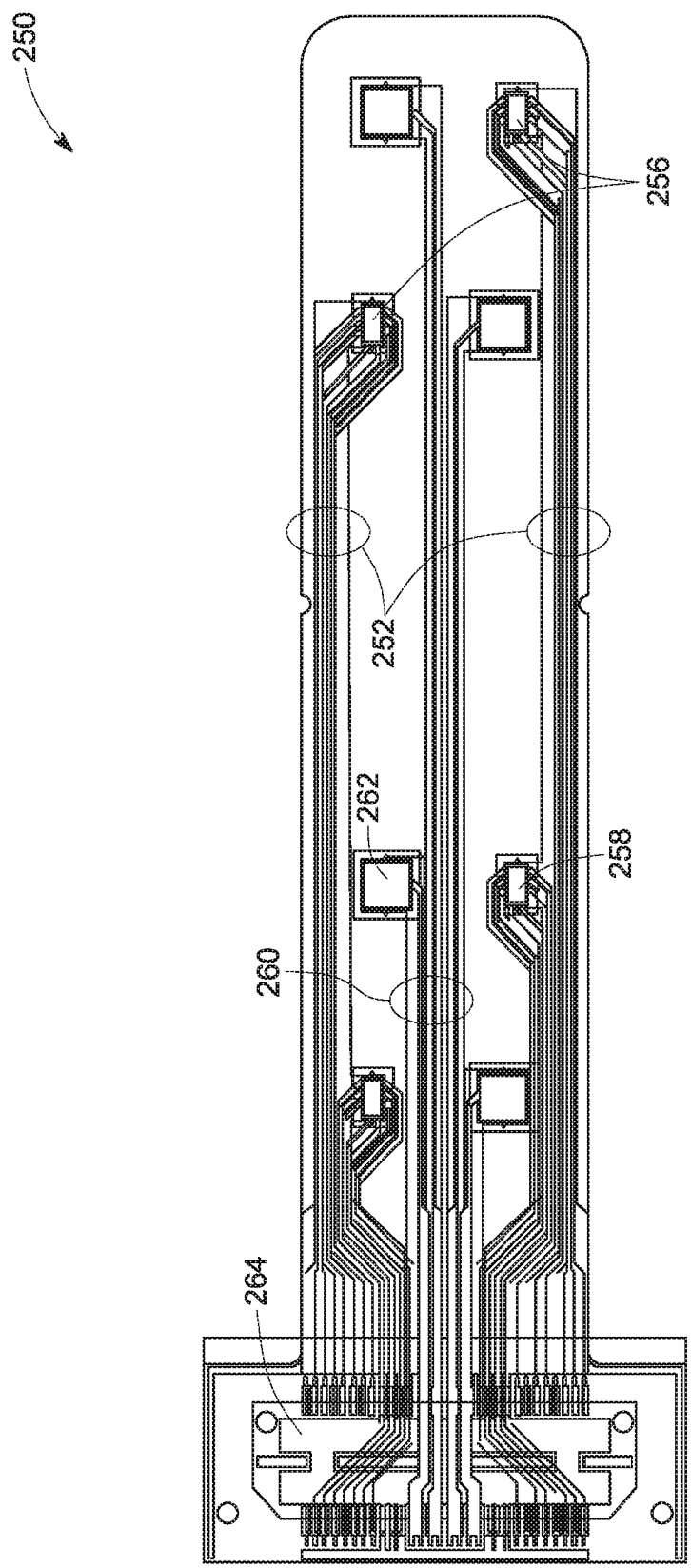
FIG. 11 is a top down view of a portion of an example pulse oximetry device having electrical connections or traces disposed between emitters of a plurality of arrays of emitters and an external connector, in accordance with aspects of the specification.

FIG. 11 illustrates an example of a portion 250 of a pulse oximetry device 250 having electrical connections or traces 252 routed between a plurality of arrays 256 of emitters 258 and an external connector 264. Further, the pulse oximetry device 250 includes electrical connections or traces 260 configured to electrically connect a plurality detectors 262 to the external connector 264. Referring to an array of emitters and a detector as a cluster, in one example, where the pulse oximetry device includes 4 such clusters, with each array of emitters having 8 emitters, the 32 emitters of the 4 clusters may be electrically coupled to an external connector such that the 32 emitters share a common anode or cathode. It may be noted that 32 traces of the 32 emitters and an additional trace for the thermally and electrically conductive layer may provide 33 electrical traces in total. Further, the pulse oximetry device 250 may include 8 traces for the 4 detectors, with each detector being connected to the external connector via 2 traces. Hence, the pulse oximetry device having 4 clusters has 41 traces. The 41 traces are coupled to the external connector 264 and exit the pulse oximetry device 250 from a single side, thereby making the device design such that the device may be conveniently coupled to an external device.

FIG. 12 illustrates a perspective view 268 of an example cable assembly 270 for operatively and electrically coupling a pulse oximetry device 272 of the specification to an external device or circuitry 274 using an external connector 276 disposed on the pulse oximetry device 272. The example cable assembly 270 may include a cable 278 having a first end 280 and a second end 282. The first end 280 of the cable 278 includes a receptor 284 which is configured to be mechanically coupled to the connector 276 to provide electrical communication between the pulse oximetry device 272 and the cable 278. The second end 282 of the cable 278 may include a cable connector 286 configured to be coupled to one or more receptors 288. The receptors 288 may be coupled to an external device, such as, but not limited to a display (not shown). In one example, the display may be configured to display oxygen saturation levels in the blood of the patient.

FIG. 13 illustrates an example pulse oximetry device 290 of the specification, where the device 290 is operatively coupled to a cable assembly 292. The pulse oximetry device 290 is disposed on a finger 291. The cable assembly 292 facilitates the coupling of the pulse oximetry device 290 to an external device 294, such as, but not limited to, a display. As illustrated, advantageously, the pulse oximetry device 290 may be disposed directly on the body, thereby providing proximity between the tissues and the emitters and detectors of the pulse oximetry device 272. Further, advantageously, the device 290 may be thin, light weight and flexible. In the illustrated embodiment, the device 290 may be a wearable and disposable device. In one example, the device 290 may be wrapped around the finger as easily as a band aid to take measurements representative of oxygen saturation in the blood.

Although not illustrated, in one embodiment, the pulse oximetry device 290 may be coupled to an external device using a wireless connection. In this embodiment, in operation, the pulse oximetry device 290 may be disposed on the patient, and a display may be disposed at a suitable distance from the pulse oximetry device and there may not be any cable running between the pulse oximetry device 290 and the display, thereby making the device very convenient to use.

Advantageously, the array of emitters may be formed on flat and non-flat surfaces with similar ease. Further, the method provides provisions for simultaneously performing one or more steps for different portions of the device substrate. The array of emitters provides a thin and flexible structure which may be employed in various applications. The thin and flexible array of emitters may be printed for applications such as healthcare, monitoring, or combinations thereof. Further, the design of the array of emitters allows dies of different polarities (anode on top vs. bottom) to be integrated into the same device. By way of example, the design of the array of emitters allows different emitters of the array of emitters to be disposed such that the anodes and electrodes may be on the same or different sides with respect to each other. Further, the pulse oximetry devices employing the plurality of arrays of the emitters of the specification may be configured to conform to a body shape as required. The plurality of arrays of the emitters may be produced using roll-to-roll processing. Further, the plurality of arrays of the emitters may be produced in high volume using in-expensive fabrication methods. For example, the method of making the plurality of arrays of the emitters may use high volume pick and place fabrication techniques along with wirebonding tools. Additionally, the flexible substrate along with the thermally and electrically conductive layer may be in expensive as compared to conventional aluminum substrates for light emitting diodes.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A pulse oximetry system, comprising:
   a pulse oximetry device comprising:
      a device substrate having a first side and a second side;
      a thermally and electrically conductive layer disposed on the first side of the device substrate;
      an interconnect layer disposed on the second side of the device substrate;
      a plurality of arrays of emitters disposed on the second side of the device substrate, wherein the plurality of arrays of the emitters is electrically coupled to the thermally and electrically conductive layer;
      a plurality of detectors disposed on the second side of the device substrate and configured to detect emission signals from one or more emitters of the plurality of arrays of the emitters;
      a plurality of wirebond contacts configured to electrically couple a portion of the interconnect layer to a corresponding emitter of the plurality of arrays of the emitters; and
   a processor configured to process the detected emission signals.

2. The pulse oximetry system of claim 1, wherein one or more emitters of the plurality of arrays of the emitters are disposed orthogonally opposite to one or more detectors of the plurality of detectors.

3. The pulse oximetry system of claim 1, wherein one or more emitters of the plurality of arrays of the emitters are disposed opposite to one or more detectors of the plurality of detectors, and wherein the one or more emitters of the plurality of arrays of the emitters are disposed in parallel to the one or more detectors of the plurality of detectors.

4. The pulse oximetry system of claim 1, wherein one or more emitters of the plurality of arrays of the emitters are disposed opposite to one or more detectors of the plurality of detectors, and wherein the one or more emitters of the plurality of arrays of the emitters are disposed in parallel and at an offset to the one or more detectors of the plurality of detectors.

5. The pulse oximetry system of claim 1, wherein the pulse oximetry device is configured to operate in a transmission mode, a reflection mode, or both.

6. The pulse oximetry system of claim 1, wherein the pulse oximetry device is configured to be disposed on one side of a body part.

7. The pulse oximetry system of claim 1, wherein the pulse oximetry device is configured to be disposed on two sides of a body part.

8. The pulse oximetry system of claim 1, wherein the pulse oximetry device is configured to conform to a shape of a body part.

9. The pulse oximetry system of claim 1, wherein the pulse oximetry device comprises an external connector.

10. The pulse oximetry system of claim 1, wherein the pulse oximetry device comprises a first plurality of electrical traces configured to provide an electrical connection to each emitter of the plurality of arrays of the emitters, and a second plurality of electrical traces configured to provide an electrical connection to each detector of the plurality of detectors.

11. The pulse oximetry system of claim 10, wherein the first plurality of electrical traces and the second plurality of electrical traces exit the device substrate from the same side of the device substrate.

12. The pulse oximetry system of claim 10, wherein the first plurality of electrical traces and the second plurality of electrical traces are coupled to an electrical connector.

13. The pulse oximetry system of claim 10, further comprising a cable assembly, wherein the cable assembly is configured to operatively couple the pulse oximetry device to an external device.

14. The pulse oximetry system of claim 13, wherein the cable assembly is operatively coupled to a display member configured to display the processed data from the processor.

15. The pulse oximetry system of claim 13, wherein the cable assembly comprises a receptor configured to operatively couple a first end of the cable assembly to an external connector.

16. The pulse oximetry system of claim 1, wherein the device substrate is configured to be disposed around at least a portion of a body part.

17. The pulse oximetry system of claim 1, wherein the pulse oximetry device and one or more of a display member and the processor are wirelessly coupled to one another.

18. The pulse oximetry system of claim 1, wherein the pulse oximetry device comprises a plurality of encapsulations, wherein one or more encapsulations of the plurality of encapsulations are configured to encapsulate one or more emitters of the plurality of arrays of the emitters.

19. The pulse oximetry system of claim 1, further comprising an encapsulation corresponding to each array of the plurality of arrays of the emitters.

\* \* \* \* \*